(12) United States Patent
Wang

(10) Patent No.: US 9,283,036 B2
(45) Date of Patent: Mar. 15, 2016

(54) LASER THERAPY APPARATUS WITH CONTROLLED OPTICAL COHERENCE

(75) Inventor: Sean Xiaolu Wang, Wilmington (DE)

(73) Assignee: BWT Property, Inc., Newark, DE (US)

( * ) Notice: Subject to any disclaimer, the term of this patent is extended or adjusted under 35 U.S.C. 154(b) by 2471 days.

(21) Appl. No.: 12/100,223

(22) Filed: Apr. 9, 2008

(65) Prior Publication Data
US 2008/0255638 A1   Oct. 16, 2008

Related U.S. Application Data

(60) Provisional application No. 60/910,855, filed on Apr. 10, 2007.

(51) Int. Cl.
*A61B 18/20* (2006.01)
*A61B 18/00* (2006.01)

(52) U.S. Cl.
CPC ....... *A61B 18/20* (2013.01); *A61B 2018/00636* (2013.01)

(58) Field of Classification Search
CPC .................................. A61B 18/20; A61N 5/06
USPC ...................... 372/9–32; 607/88–89
See application file for complete search history.

(56) References Cited

U.S. PATENT DOCUMENTS

| | | | |
|---|---|---|---|
| 5,485,481 A * | 1/1996 | Ventrudo et al. | 372/6 |
| 6,058,128 A * | 5/2000 | Ventrudo | 372/96 |
| 6,690,474 B1 * | 2/2004 | Shirley | 356/603 |
| 6,710,914 B2 * | 3/2004 | Arbore et al. | 359/330 |
| 7,054,339 B1 * | 5/2006 | Hu et al. | 372/12 |
| 2005/0047454 A1 * | 3/2005 | Williamson, III | 372/26 |

OTHER PUBLICATIONS

A N Rubinov, Physical grounds for biological effect of laser radiation, Sep. 17, 2003, J. Phys. D: Appl. Phys. 36, p. 2317-2330.*

* cited by examiner

*Primary Examiner* — Lynsey Crandall

(57) ABSTRACT

A laser therapy method and apparatus is disclosed. The optical coherence property of the therapy laser is actively controlled to provide optimum therapy results for difference types of biological tissue and body parts.

27 Claims, 2 Drawing Sheets

LASER THERAPY APPARATUS WITH CONTROLLED OPTICAL COHERENCE

REFERENCE TO RELATED APPLICATIONS

This application claims an invention which was disclosed in Provisional Patent Application No. 60/910,855, filed Apr. 10, 2007, entitled "Laser Therapy Apparatus with Controlled Optical Coherence." The benefit under 35 USC §119(e) of the above mentioned U.S. Provisional applications is hereby claimed, and the aforementioned applications are hereby incorporated herein by reference.

FIELD OF THE INVENTION

This invention generally relates to a laser therapy apparatus and more specifically to a laser therapy apparatus with controlled optical coherence.

BACKGROUND

Coherence has been perceived to perform an important role in laser therapy comprising laser bio-modulation, laser bio-stimulation, etc. Studies have shown that a highly coherent laser in some cases is more effective than light emitting diodes (LEDs) or other type of lasers which have lower degree of optical coherence. The previously disclosed laser therapy apparatus merely uses whatever laser that is available. For example, semiconductor laser diodes (LDs) are typically used due to their low cost and commercial availability. These lasers have various degrees of optical coherences which may not be optimized for a particular modality or effectiveness associated with the treatment of a particular tissue type or body part. In addition, their optical coherence property can change with ambient conditions such as temperature, optical delivery systems, etc. This coherence change can induce unpredictable treatment results.

Furthermore, continuous scanning scheme of the laser beam is generally employed in the prior arts, in which the effect of intensity gradient created by speckle or interference is diminished due to overlapping by multiple paths within relative short time gaps.

There thus exists a need for a laser therapy apparatus with controlled optical coherence to produce a consistent and optimized therapeutic result.

SUMMARY OF THE INVENTION

It is thus the overall goal of the present invention to provide a therapy laser apparatus with controlled optical coherence property. According to one aspect of the present invention, the therapy laser apparatus comprises a laser diode with its output spectrum narrowed and stabilized by a volume Bragg grating to produce a highly polarized laser beam with relative long and stable coherence length.

According to another aspect of the present invention, the coherence length of the therapy laser is actively controlled through a modulation scheme.

According to yet another aspect of the present invention, the laser beam is applied to the subject tissue in a stationary manner during a specific therapeutic time to maximize the effect of optical coherence.

A method for making an optimized laser therapy device for a subject biological tissue is provided. The method comprising the steps of: providing a laser element to produce a laser beam; causing the laser beam to enter the biological tissue and produce an interference induced speckle pattern of intensity; and controlling a coherence length of the laser beam to control the dimensions of the speckle pattern so as to achieve an optimized laser therapy result.

A method for making an optimized laser therapy device for a subject biological tissue is provided. The method comprising the steps of: providing a laser element to produce at least two laser beams; causing the laser beams to enter the biological tissue and produce an interference pattern of intensity; and controlling a coherence length of the laser beams and an angle between the laser beams to control the dimensions of the interference pattern as to achieve an optimized laser therapy result.

An optimized laser therapy device for a subject biological tissue using the above methods is provided.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
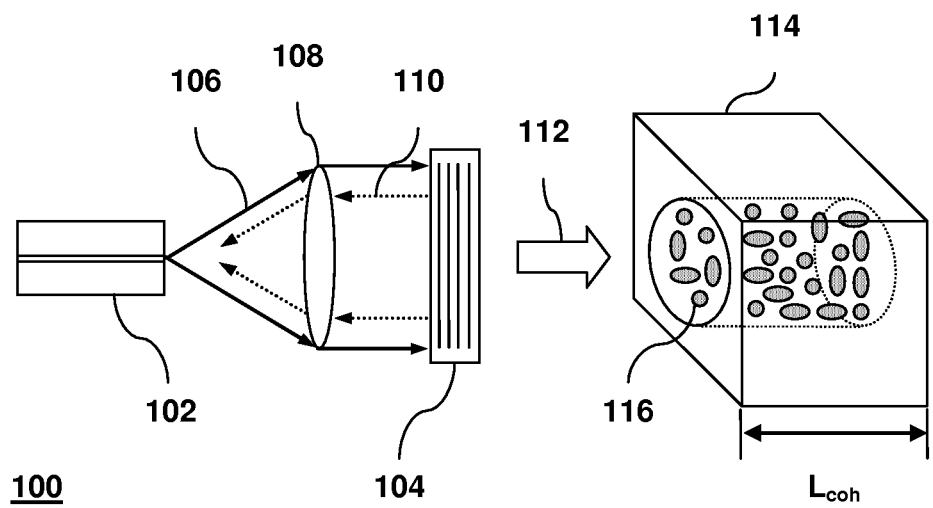
FIG. 1 shows one exemplary embodiment of the laser therapy apparatus which comprises a semiconductor laser diode.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser therapy apparatus with controlled coherence. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In one preferred embodiment of the present invention as shown in FIG. 1, the laser therapy apparatus 100 comprises at least one semiconductor laser diode 102 with its output spectrum controlled and stabilized by a volume Bragg grating 104. The laser diode 102 can be a broad area laser diode to provide high output power, or a single transverse mode laser diode to provide good beam quality and narrow spectral linewidth. The output light beam 106 of the laser diode 102 is first collimated by a lens 108 and then delivered onto the volume Bragg grating 104, which acts as an external cavity. The volume Bragg grating 104 reflects a portion of the light beam 106 back into the internal cavity of the laser diode 102, where the wavelength of the reflected beam 110 falls within a narrow bandwidth around the Bragg wavelength of the grating 104. The reflected light beam 110 functions as a seed to lock the lasing wavelength of the laser diode 102 to the Bragg wavelength of the grating. The disclosed external cavity technology is capable of reducing the linewidth of the laser diode by several orders of magnitude. Since the coherence length of the laser is inversely proportional to its spectral linewidth, the optical coherence of the wavelength-locked laser diode is greatly enhanced therefore. In the mean time, the output spectrum of the laser diode 102 is stabilized and locked by the volume Bragg grating 104. Thus the coherence property of the laser diode will not vary with ambient temperature, an important factor in the production of a consistent laser therapy result. By selecting proper bandwidth for the volume Bragg grating, the coherence length of the wavelength-locked laser can be controlled to a value ranging from sub-millimeters to several meters. As can be seen, the present invention contemplates controlling the optical coherence property of the laser diode with an external cavity structure formed by a volume Bragg grating.

When the output light beam 112 of such a coherence enhanced laser diode is applied onto a subject biological tissue 114, the light beam is scattered into various directions. The random interference of light waves of various directions occurs over the entire coherence length ($L_{coh}$) in the tissue. As a result, a speckle pattern 116 of intensity is produced. Maximum value of the intensity appears at the random constructive interference. The minimum value occurs at the random destructive interference. The enhanced optical coherence of the laser diode results in a highly polarized light beam, which facilitates the production of a speckle pattern with strong intensity contrast. These coherence induced speckles 116 cause a spatially inhomogeneous deposition of light energy and lead to statistically inhomogeneous photochemical processes, e.g. increase of ATPase (adenosine triphosphatase) and activation of enzymes, increases in temperature, changes in local pressure, deformation of cellular membranes, etc. The dimensions of these speckles are determined by the coherence length of the laser diode. Through an active coherence control scheme as shown in FIG. 2, the speckle pattern can be controlled to produce optimum or desired laser therapy results for different tissue types and body parts.

Figure 2:
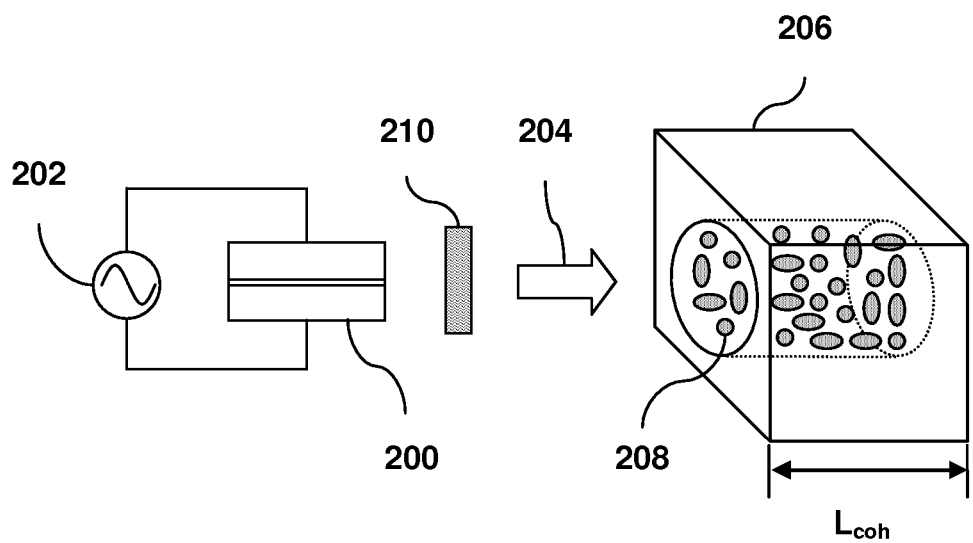
FIG. 2 shows another exemplary embodiment of the laser therapy apparatus, where the optical coherence property of the therapy laser is actively controlled through a modulation scheme.

Referring to FIG. 2, the optical coherence property of the therapy laser 200 is controlled with a pulsed modulation scheme. Here the therapy laser can be a wavelength-locked laser diode as disclosed in FIG. 1, or a thermal-cooled DFB (distributed feed-back), DBR (distributed Bragg-reflector) or even FP (Febry-Perot) laser diode with a stable coherence property. In FIG. 2, an RF (radio frequency) modulator 202 is employed to apply a high frequency pulsed modulation on the drive current of the laser diode 200, which can effectively broaden the linewidth of the laser diode and reduce its coherence length. One of the effective broadening mechanisms is self-sustained pulsation as disclosed in U.S. Pat. No. 5,519,263 to Guifang Li et al., which is hereby incorporated herein by reference. By adjusting the modulation frequency, the coherence length of the therapy laser 200 can be actively controlled. Thus the laser beam 204 produces a speckle pattern 208 with desired dimensions in the subject tissue 206. When the dimension of the speckle pattern matches with the cellular size of the tissue, an optimum therapy result is achieved. It is noted herein that the coherence control method is not limited to the pulsed modulation scheme as disclosed above. Any modulation scheme that can control the linewidth of the therapy laser, such as those active Q-switching and mode-locking techniques, can be applied without exceeding the scope of this invention. Another approach is to incorporate additional optical component 210 in the beam delivery optics. The additional optical component 210 comprises such devices as diffractive, reflective, or diffusive optical components. Further optical component 210 may comprise a phase modulation mechanism that alters the coherence length of the laser beam 204 thereby altering the speckle pattern 208 produced therefore.

Figure 3:
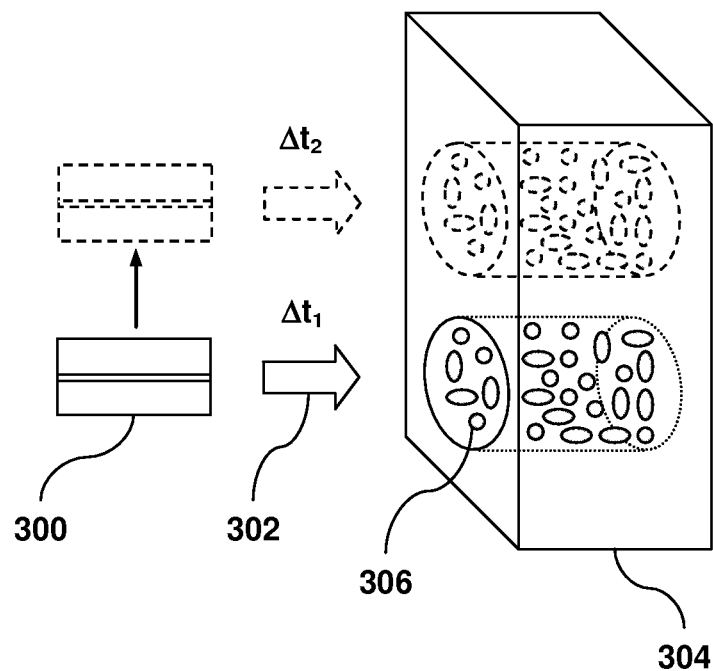
FIG. 3 illustrates a stationary treatment scheme to maximize the coherence effect of the therapy laser.

Referring to FIG. 3, a stationary illumination scheme is disclosed to maximize the coherence effect of the therapy laser 300, where the laser beam 302 produces a stable speckle pattern 306 in the subject tissue 304 during one treatment session. In this scheme, the laser beam is first positioned to illuminate a first portion of the subject tissue for an illumination time of $\Delta t_1$. Due to its relatively high spatial coherence, the laser beam 302 from the therapy laser 300 can be focused to a small beam diameter, thus producing high power intensity. The illumination time ($\Delta t_1$) of the laser beam can then be reduced to avoid any disturbance of the speckle pattern 306 caused by inadvertent shift in the relative position of the laser beam 302 and the subject tissue 304. In a subsequent time period ($\Delta t_2$), the laser beam is shifted to illuminate another portion of the subject tissue which does not overlap with the previous treatment area. The same procedure is repeated until the whole subject tissue area is treated to complete one treatment session. This mapped stationary illumination scheme produces a highly gradient intensity distribution in comparison with those known continuous scanning schemes employed in the prior arts, in which the effect of intensity gradient created by speckle or interference is diminished due to overlapping by multiple paths within relative short time gaps. Thus the effect of optical coherence of the present invention is maximized over known continuous scanning schemes.

Figure 4:
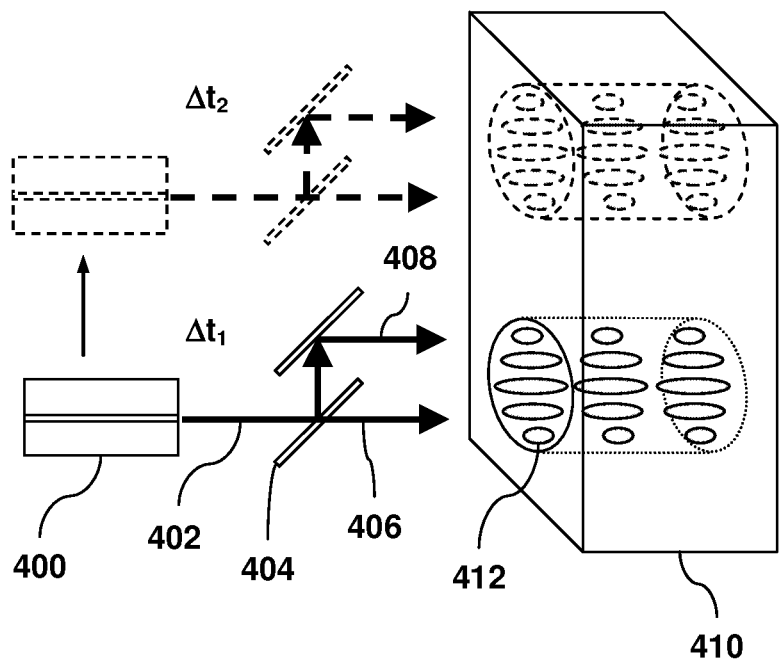
FIG. 4 illustrates a variation of FIG. 3.

In a slight variation of the embodiment as show in FIG. 4, the laser beam 402 from the therapy laser 400 is first split into two beams, i.e. beam 406 and beam 408 by a beam splitter 404. The two laser beams (406 and 408) interfere in the subject tissue 410 to produce an interference pattern 412 similar to the speckle pattern 306 as shown in FIG. 3. This interference pattern 412 causes spatially inhomogeneous deposition of light energy and lead to statistically inhomogeneous photochemical processes. The interference pattern 412 is less irregular than the speckle pattern. In addition, the dimensions of the interference pattern 412 can be controlled by controlling the angle between the two laser beams 406 and 408. The illumination time and the position of the two laser beams can be controlled in a similar manner as the mapped stationary illumination scheme disclosed in FIG. 3 to produce a highly gradient light intensity distribution.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for using an optimized laser therapy device for a subject biological tissue, the method comprising the steps of:
   providing a laser element to produce a laser beam;
   causing the laser beam to enter the biological tissue and produce an interference induced speckle pattern of intensity; and
   controlling a coherence length of the laser beam to control the dimensions of the speckle pattern so as to achieve an optimized laser therapy result.

2. The method of claim 1, wherein the laser element comprises a semiconductor laser diode.

3. The method of claim 2, wherein the coherence length of the laser beam is controlled by controlling a spectral linewidth of said laser diode with an external cavity.

4. The method of claim 3, wherein the external cavity comprises a wavelength-selective element.

5. The method of claim 4, wherein the wavelength-selective element comprises a volume Bragg grating.

6. The method of claim 1, wherein the coherence length of the laser beam is controlled by applying a modulation scheme onto the laser element to control a spectral linewidth of said laser element.

7. The method of claim 1, wherein the coherence length of the laser beam is controlled by an optical component positioned in a path of the laser beam.

8. The method of claim 1, further comprising a step of controlling an illumination time and a physical position of the laser beam.

9. The method of claim 1, wherein the speckle pattern induces spatially inhomogeneous photochemical processes.

10. A method for using an optimized laser therapy device for a subject biological tissue, the method comprising the steps of:
    providing a laser element to produce at least two laser beams;
    causing the laser beams to enter the biological tissue and produce an interference pattern of intensity; and
    controlling a coherence length of the laser beams and an angle between the laser beams to control the dimensions of the interference pattern as to achieve an optimized laser therapy result.

11. The method of claim 10, further comprising a step of controlling an illumination time and a physical position of the laser beams.

12. The method of claim 10, wherein the laser element comprises a semiconductor laser diode.

13. The method of claim 10, wherein the coherence length of the laser beam is controlled by controlling a spectral linewidth of said laser diode with an external cavity.

14. The method of claim 13, wherein the external cavity comprises a wavelength-selective element.

15. The method of claim 14, wherein the wavelength-selective element comprises a volume Bragg grating.

16. The method of claim 10, wherein the coherence length of the laser beam is controlled by applying a modulation scheme onto the laser element to control a spectral linewidth of said laser element.

17. The method of claim 10, wherein the coherence length of the laser beam is controlled by an optical component positioned in a path of the laser beam.

18. The method of claim 10, wherein the interference pattern induces spatially inhomogeneous photochemical processes.

19. An optimized laser therapy device for a subject biological tissue comprising:
    means for producing at least one laser beam;
    means for causing the at least one laser beam to enter the biological tissue and produce an interference pattern of intensity; and
    means for controlling a coherence length of the at least one laser beam to control the dimensions of the interference pattern as to achieve an optimized laser therapy result.

20. The device of claim 19, further comprising means for controlling an illumination time and a physical position of the laser beams.

21. The device of claim 19, wherein the laser element comprises a semiconductor laser diode.

22. The device of claim 19, wherein the coherence length of the laser beam is controlled by controlling a spectral linewidth of said laser diode with an external cavity.

23. The device of claim 22, wherein the external cavity comprises a wavelength-selective element.

24. The device of claim 23, wherein the wavelength-selective element comprises a volume Bragg grating.

25. The device of claim 19, wherein the coherence length of the laser beam is controlled by applying a modulation scheme onto the laser element to control a spectral linewidth of said laser element.

26. The device of claim 19, wherein the coherence length of the laser beam is controlled by an optical component positioned in a path of the laser beam.

27. The device of claim 19, wherein the interference pattern induces spatially inhomogeneous photochemical processes.

* * * * *